United States Patent [19]

Seo et al.

[11] Patent Number: 5,824,840
[45] Date of Patent: Oct. 20, 1998

[54] DIABETES-INDUCING TRANSGENIC MOUSE

[75] Inventors: Jeong-Sun Seo; Soonhee Kim; Jongil Kim, all of Seoul, Rep. of Korea

[73] Assignee: Jeongsun Seo, Seoul, Rep. of Korea

[21] Appl. No.: 558,719

[22] Filed: Nov. 16, 1995

[30] Foreign Application Priority Data

Nov. 21, 1994 [KR] Rep. of Korea ............... 94-30676

[51] Int. Cl.$^6$ ............... C12N 5/00; C12N 15/00; C12N 15/09
[52] U.S. Cl. ............... 800/2; 435/172.3; 435/69.1; 435/69.7; 435/69.6; 435/91.2; 435/320.1; 536/23.1; 536/23.5; 536/24.31; 935/23; 935/78; 935/79; 935/70; 935/71
[58] Field of Search ............... 800/2; 435/172.6, 435/69.1, 69.7, 69.6, 91.2, 320.1; 536/23.1, 23.5, 24.31; 935/23, 78, 79, 70, 71

[56] References Cited

U.S. PATENT DOCUMENTS

| 5,087,571 | 2/1992 | Leder et al. | 435/240.2 |
| 5,175,383 | 12/1992 | Leder et al. | 800/2 |
| 5,175,384 | 12/1992 | Krimpenfort et al. | 800/2 |
| 5,175,385 | 12/1992 | Wagner | 800/2 |

OTHER PUBLICATIONS

Sarvetnick et al., Cell, vol. 52, pp. 773–782, Mar. 11, 1988.

Hunt et al., Proclamation of the National Academy of Sciences, vol. 82, pp. 6455–6459, 1985.

Uney et al., Society for Neuroscience Abstracts, vol. 18, p. 1145, 1992.

Primary Examiner—Jasemine C. Chambers
Assistant Examiner—Jill D. Schmuck
Attorney, Agent, or Firm—Nixon & Vanderhye P.C.

[57] ABSTRACT

Disclosed in this invention is a transgenic mouse containing rcombinant DNA including a promoter and a heat shock protein 70 gene attached to downstream of the promoter. Transgenic mice line inducing non-insulin dependent diabetes having a blood glucose level of 300 mg/dl was obtained.

6 Claims, 5 Drawing Sheets

DIABETES-INDUCING TRANSGENIC MOUSE

BACKGROUND OF THE INVENTION

1. Field of the Invention

The present invention relates to a diabetes-inducing transgenic mouse, more specifically, to a diabetes-inducing transgenic mouse which is generated by inserting a gene to expressing heat shock protein (Hsp) under the control of an insulin promoter to a mouse.

2. Description of the Related Arts

A transgenic mouse is created by microinjecting a specific gene fragment to a fertilized egg of a mouse and introducing it to the uterus of a mother mouse to give birth to offspring. By screening the DNA taken from tail of the mouse 3 weeks after birth, it can be confirmed that the gene is inserted to DNA in the cell of the offspring. A transgenic mouse is applicable to detect functions of a gene in vivo. The transgenic mouse can be used as a model for many human diseases and as a bio-reactor which produces required genes, and also can be used for developing medicines against diseases.

Recently, the transgenic mouse technique has been developed as an approach to solve various genetic problems, such as tumor. The success of producing a c-myc oncogene-inserted transgenic mouse by P. Leder at Harvard University in the U.S.A. has drawn great attention in the field of leukemia in the human body, and a patent for the first time, for a living organism was issued based on this technique (U.S. Pat. No. 5,087,571). Male mouse for investigating prostatic disease is disclosed in U.S. Pat. No. 5,175,383 to Philip Leader, a mouse which cannot produce mature T-cells is disclosed in U.S. Pat. No. 5,175,384 to Paulus J. A. Krimpenfort et al., and a mouse which produces human B interferon is disclosed in U.S. Pat. No. 5,175,385 to Thomas E, Wagner et al.

Insulin which is secreted from the B cell of pancreas islets is a hormone which controls the level of glucose in blood. Diabetes is a metabolism disorder resulting from the lack of insulin secretion thereby limiting the carbohydrate, lipid and protein. Diabetes and complication thereof are the third leading cause of death in the United States, affecting nearly 5% of the population and are very common diseases in the world. The number of diabetes patients has been increasing in number.

Diabetes can be classified broadly into insulin dependent diabetes (type I) and non-insulin dependent diabetes (type II). Owing to autoimmune disorder or non-reproduction of damaged P cells, insulin dependent diabetes needs supply of insulin which is produced outside of the human body and furthermore, juveniles suffer from the insulin dependent diabetes. Non-insulin dependent diabetes are caused by insufficiency of insulin acceptor and decrease of insulin binding in the organism although insulin is adequately or excessively secreted from the human body. They occur at a low rate and symptoms thereof are relatively minor. Therefore, insulin dependent diabetes represent only 5 to 10% of all cases, and the rest belong to non-insulin dependent diabetes.

In the meantime, heat shock protein (Hsp) is an important protein in recovering damaged cells, and is expressed in the state of heat shock or stress, at an embryonic stage as well as at a special step of cell differentiation and cell cycle.

The inventors have conducted research on the influences of Hsp expression on differentiation of B cells of pancreas islets. The inventors have discovered that when a gene containing heat shock protein was combined with a human insulin promoter and transferred to a mouse, the mouse developed diabetes. Thus, the present invention has been accomplished.

SUMMARY OF THE INVENTION

Accordingly, an object of this invention is to provide a diabetes-inducing transgenic mouse, which is generated by rearranging human heat shock protein gene and human insulin promoter, to a mouse.

In order to achieve the object, the present invention provides a recombinant DNA for preparing a transgenic animal, preferably a mouse, expressing symptoms associated with non-insulin dependent diabetes, such as increased blood glucose levels and excessively proliferated pancreas, comprising a 1.8 kbEcoRI-BamHI fragment of human insulin promoter of human insulin gene; and a 2.KBkb BamHI-HindIII fragment of human heat shock protein 70 gene operably linked to, and downstream of, said fragment of promoter. Further, a transgenic comprising the recombinant DNA and expressing the recombinant DNA gene product in its germ cells and somatic cells, wherein the transgenic mouse exhibits symptoms associated with non-insulin dependent diabetes, such as increased blood glucose levels and excessively proliferated pancreas.

Furthermore, the present invention provides a process for preparing a transgenic animal, preferably a mouse, comprising the steps of inserting a recombinant DNA including a 1. KBkb EcoRI-BamHI fragment of human insulin promoter of a human insulin gene and a 2. KBkb BamHI-HindIII fragment of heat shock protein 70 gene operably linked to, and downstream of, said fragment of promoter into a fertilized egg; transferring said fertilized egg into a foster mother mouse; and obtaining a founder mouse whose offspring expresses the recombinant DNA gene product in its germ cells and somatic cells.

The transegenic animal is selected from a group consisting of a mouse, a pig and a chicken.

The recombinant DNA is inserted into said fertilized egg of the animal, such as a mouse, at the embryonic stage.

In this invention, the process for preparing a transgenic mouse further comprises the steps of mating a founder mouse with a normal mouse to obtain a F1 transgenic mouse; and mating said F1 transgenic mice expressing the recombinant DNA gene product in its germ cells and somatic cells, among said F1 mice to obtain homozygote F. mouse.

Transgenic mice line inducing non-insulin dependent diabetes having a blood glucose level of at least 300 mg/dl can be obtained by said method, which is useful in the fields of research and development of models of diabetes, identification of mechanism inducing diabetes, development of therapeutic agents and assays for novel medicines.

DETAILED DESCRIPTION OF THE EMBODIMENT

Figure 1:
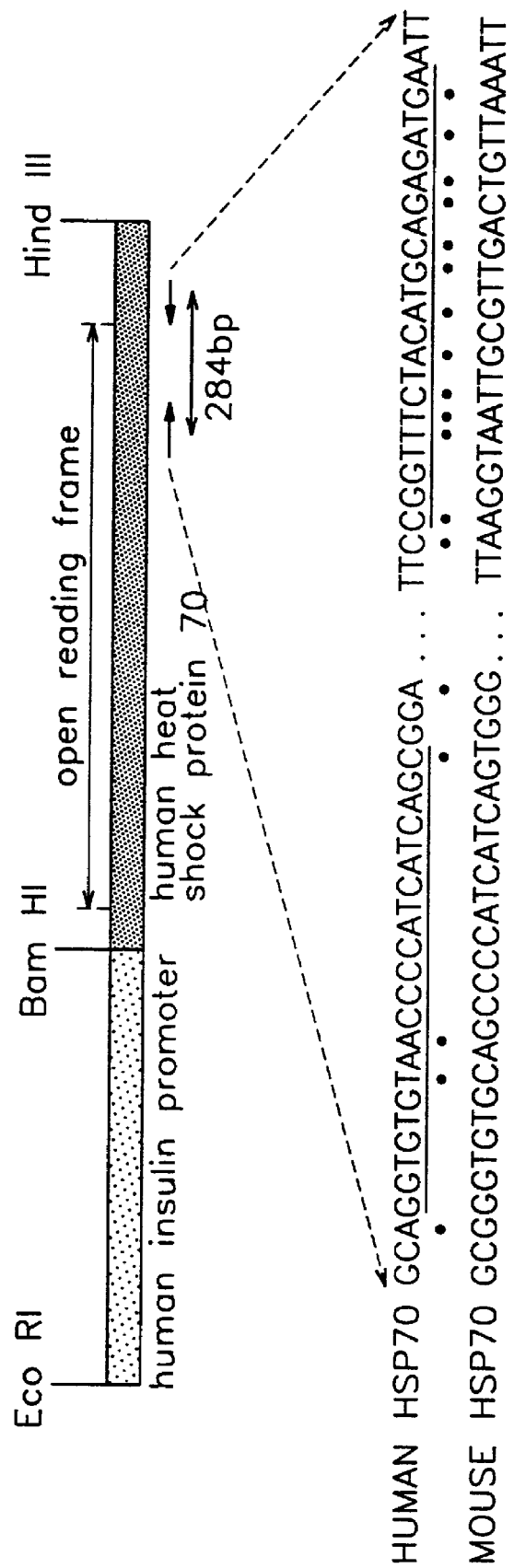
FIG. 1 is a schematic representation of a gene which is constructed to express human heat shock protein 70 under the control of insulin promoter.

The present invention is further explained in more detail with reference to the following example which does not necessarily limit this invention.

Step 1: Construction of Human Heat Shock Protein Expression Vector

In order to obtain human heat shock protein, pH2.3 (Hunt, C. & Morimoto, R. I., 1985, Proc, Natl.Acad. Sci. 82) was digested with BamHI and HindIII restriction enzyme to obtain 2.3 KB DNA fragment.

pSP65INS (N. Sarvetnick et al., 1988, Cell vol.52, 773–7882) was treated with EcoRI and BamHI restriction enzyme to obtain 1.8 kb human insulin promoter. Two fragments were ligated to obtain 4.1 KB fragment FIG. 1) and the fragment was cloned on EcoRI and HindIII restriction enzyme site of pSP65 purchased from Promega to prepare pINS/HSP FIG. 2), and then the pINS/HSP was introduced into HB 101 E. coli to obtain transformed strains. In order to prepare DNA solution for microinjection, the E. coli was inoculated with LB medium (1% Bactotrypton, 0.5% Yeast Extract, 1% NaCl) containing ampicillin, cultured at a temperature of 37° C. overnight. The culture was collected by centrifuging the solution at 2000 g for 10 minutes, and dissolving in a solution containing 50 mM glucose, 10 mM Tris-Cl, 1 mM EDTA, 4 mg/ml lysozyme, and allowing same to incubate for 5 minutes in an ice bath. After 0.2N NAOH, 2 volume of 1% SDS solution were cautiously mixed with the resulting solution, the mixture was shaken and allowed to settle at room temperature for 5 minutes. Thereafter, 0.5 volumes of 5M potassium acetate solution was added to the solution, and the obtained mixture was allowed in an ice bath, and centrifuged at 12,000 for 10 minutes to obtain supernatant. The supernatant was extracted two or three times with phenol and phenol/chroloform/isoamylalcohol (28:24:1), and plasmid DNA was precipitated by adding 0.1 volumes of 3M sodium acetate and 2 volumes of ethanol to the extract. The precipitated DNA was dissolved in TE buffer solution (10 mM Tris-Cl, pH 8.0/1 mM EDTA, pH 8.0), and CsCl was added to the solution to have 1 g/ml of final concentration of CsCl. The solution was centrifiged at 100,000 rpm for 12 hours by Beckman TL 100 roter to obtain purified plasmid DNA. The band with the plasmid DNA was separated using a syringe, extracted with n-butanol, dialysed against TE buffer solution for 24 hours. After plasmid DNA extraction, DNA was digested with Hind III restriction enzyme, and electrophoresed through 0.8% agarose gel, and DNA was purified by cutting the agarose gel fragment containing 4.1 KB DNA inducing diabetes. The concentration of the DNA was determined, and then the DNA was diluted with the TE buffer solution containing 10 mM of tris-Cl, pH 7.5/0.2 mM EDTA, pH 8.0 to concentration of DNA of 4 ng/ul, and the DNA stored at a temperature of −20° C. and used for microinjection.

Step 2: Microinjection of Gene of Diabetes

A female mouse over 6 weeks old was selected among F1 hybrid strains (C57BL X CBA) which were purchased from Korean Life Engineering Research Institute or FVB mouse which was purchased from B&K (Great Britain), superovulated to obtain a great number of fertilized eggs from a few of donor mice. The optimum time to microinject DNA into the male pronucleus of a fertilized egg is 1 cell cycle of a fertilized egg of a mouse, and the time depended upon strain, on supplier and light-dark cycle of animal room. The light-dark cycle of animal room was set to be turned off at 7:00 p.m. and turned on at 6:00 a.m., and microinjection was usually started at 10:30 a.m. using F1 hybrid strain. One of the fertilized eggs was fixed at a position where the male pronucleus can be seen easily, and about 1–2 pl of DNA was injected into the male pronucleus with a pipet for injection.

Step 3: Insertion of Microinjected Fertilized Egg into the Oviduct of Foster Mother Mouse The fertilized eggs in which DNA were inserted were classified into healthy fertilized eggs, and dissolved eggs and then the dissolved eggs were removed. The healthy eggs were transferred to a foster mother mouse on the same day or added to MI6 medium and cultured in an incubator at a temperature of 37° C. ICR inbred strain was used as a male mouse which had mated with the foster mother mouse. The male mouse had a vasectomy, was used after ascertaining that an offspring was not brought forth in spite of having the vaginal plug when it was mated with another female mouse. An ICR female mouse close to ovulation period was mated with a male mouse which had a vasectomy, and if the female has vaginal plug, the female mouse was used as a foster mother mouse. 0.2 ml of an anaesthetic which is somopentyl (Pitman-Moor Co., 64.8 mg sodium pentobarbital/ml) diluted 10 times with PBS was inserted into the abdominal cavity. Then 20 to 25 of fertilized eggs, to which DNA were microinjected were inserted into both oviducts of the foster mother mouse, and the operated site was sutured.

Step 4: Breeding of Transgenic Mouse

After confirming insertion of gene inducing diabetes into transgenic mouse using DNA taken from the tail by PCR, the transgenic mouse was mated with a normal hybrid mouse (C57BL X CBA) or FVB inbred mouse which were more than 6 weeks of age. Every morning, the vaginal plug was examined to determine whether it had been fertilized. In case of abnormal mating, a normal mouse was mated with another mouse to continuously examine whether it had been fertilized. In 3 to 4 weeks after birth (F1) of offspring, an offspring was analyzed using DNA taken from the tail by PCR. After confirming the transfer of gene inducing diabetes of the foster female into the offspring, the offspring was considered a transgenic mice line. Again at 6 weeks of age, the F1 transgenic mouse was mated with a normal hybrid mouse (C57BL X CBA) or FVB inbred mouse.

In order to generate a homozygote transgenic mouse, two mice which were inbreeded from the foster mother mouse among F1 transgenic mice were mated with each other. In order to detect a homozygote mouse among F. transgenic mice which were born from the mice, the F. transgenic mouse was mated with a normal hybrid (C57BL X CBA) mouse or an FVB inbred mouse to generate an F3 mouse. It was examined whether the F3 mouse had gene inducing diabetes or not.

Analysis of Diabetes-Inducing Transgenic Mouse

1) Extraction of DNA taken from tail

A polymer DNA was extracted from the tail of the mouse. The extract was analyzed by PCR method to examine whether the mouse had transgenic genes or not.

1.5 to 2.0 cm tail section of a 3 to 4 week old mouse was cut off, minced, and added to 500 ul of TE buffer solution containing 50 mM Tris-Cl, pH 8.0, 50 mM EDTA, pH 8.0, 0.5% SDS. Proteinase K was added to the resultant to make concentration of 200 ug/ml and the mixture was reacted at a temperature of 55° C. for 9 hours. The reactant was extracted three times with an equal volume of phenol and phenol/chroloform/isoamyl alcohol (25:24:1), dialysed against 10 mM Tris-Cl, pH 8.0, 0.1 mM EDTA, pH 8.0 for 36 hours (12 hours×three times). The DNA concentration was determined using a spectrophotometer and this DNA solution was stored at a temperature of 4° C.

Figure 2:
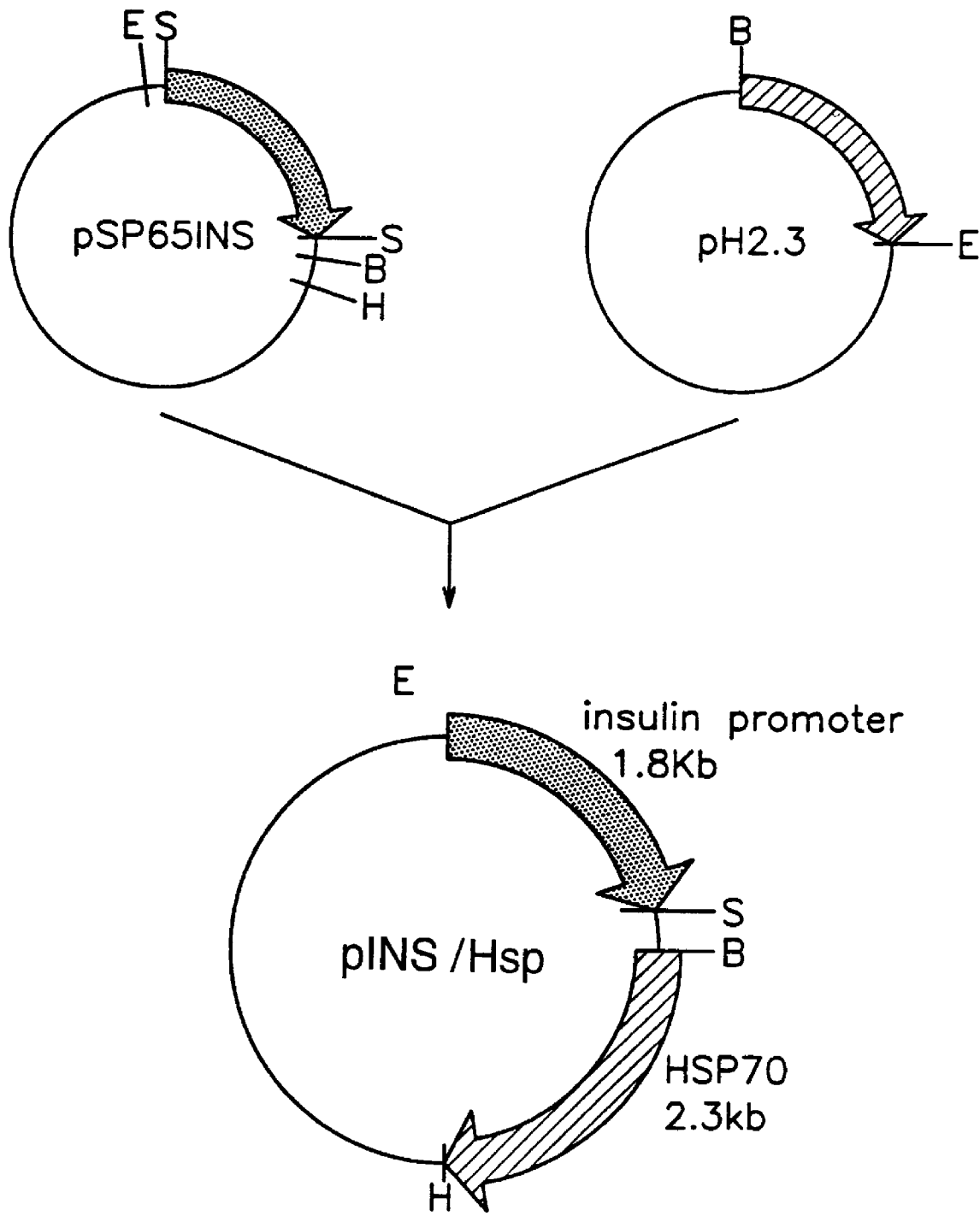
FIG. 2 is a schematic diagram showing the procedure for construction of an expression vector(pINS/HSP) human heat shock protein 70 gene.

2) Analysis of PCR 77.5 ul of deionized water, 2 ul of sample DNA, each 2 ul of dATP, dGTP, dCTP, dTTP, 10 ul of Taq DNA polymerase buffer (100 mM Tris (pH 8.3), 500 mM KCl, 15 mM $MgCl_2$ 0.1% gelatin) and 2 ul of the primer were added to a microfuge tube and mixed. The zone indicated as arrows in FIG. 1 represents the primer, and the underlined zone represents base sequence of the primer. Mineral oil was added to the supernatant of the mixture, and the solution was heated at a temperature of 95° C. for 5 minutes to inactivate protease remaining at DNA extraction solution and DNA was denatured, and the temperature was changed to 75° C. 0.5 ul of Taq DNA polymerase (2.5 U) was added to the mixture in each tube by passing through oil layer and mixed. Thereafter, PCR cycle was carried out as follows: The mixture was denaturated at a temperature of 94° C. for 0.5 to 1 minute, annealed at a temperature of 55° C. for 0.5 to 1 minute and then extended at a temperature of 72° C. for 1 minute. This cycle was repeated 30 times. After completion of the PCR cycle, the final cycle was prolonged for 5 minutes so that the amplified DNA fragments to fully form a double strand and oil layer of supernatant of the tube was discarded, and then an equal volume of chroloform was mixed to the resultant. The mixture was centrifuged at 15,000 rpm for 5 minutes. The supernatant was transferred to a new tube and 0.1 times of 3M NaOAc (pH5.2)and 2.5 times of 95% EtOH were added to the tube, mixed, and then the mixture was cooled at a temperature of −70° C. for 15 minutes and then centrifuged at 15,000 rpm, at a temperature of 4° C. for 15 minutes to obtain precipitate. The precipitates were rinsed with 70% ETOH, and centrifuged for 5 minutes. The final PCR amplified DNA was dried under vacuum, dissolved in 20 ul of TE buffer solution or distilled water and then 1 to 2 ul of the product was electrophoresed.

Figure 3:
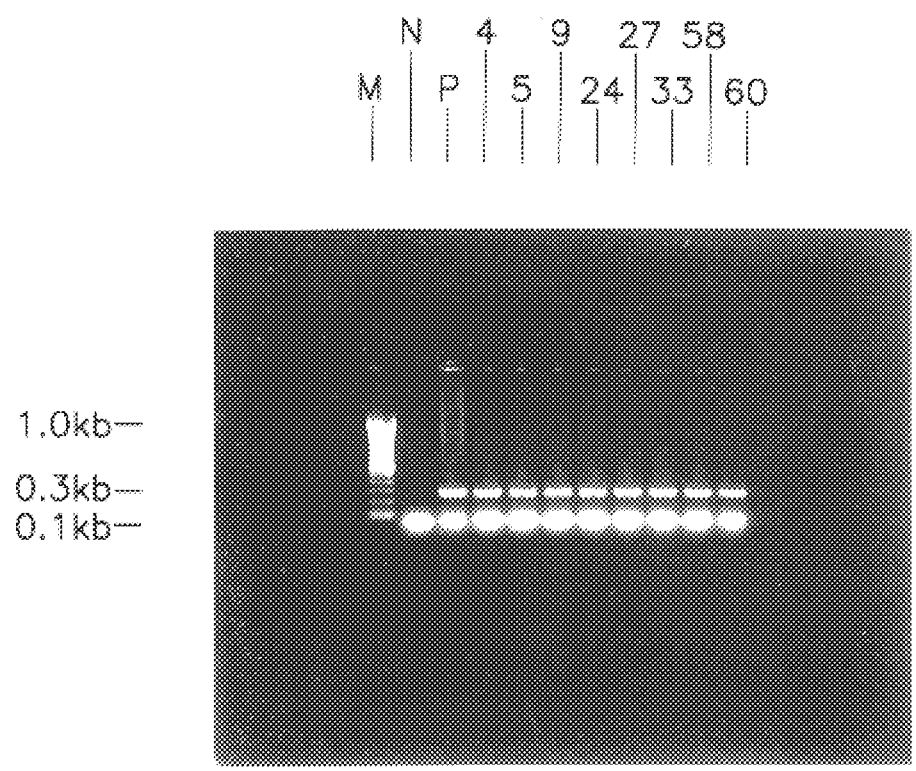
FIG. 3 shows the results of analysis of the DNA taken from the tail of a transgenic mouse by PCR.

The results of the experiment is shown in FIG. 3.In FIG. 3, M represents 100 base pair ladder, N represents negative control group and P represents positive control group. Transgenic mice numbering 4, 50, 9, 24, 33, 58 and 60 showed the same bond as that in the positive control group. Therefore, it can be seen that the gene inducing diabetes was transferred into the mouse.

3) Glucose tolerance test

Figure 4:
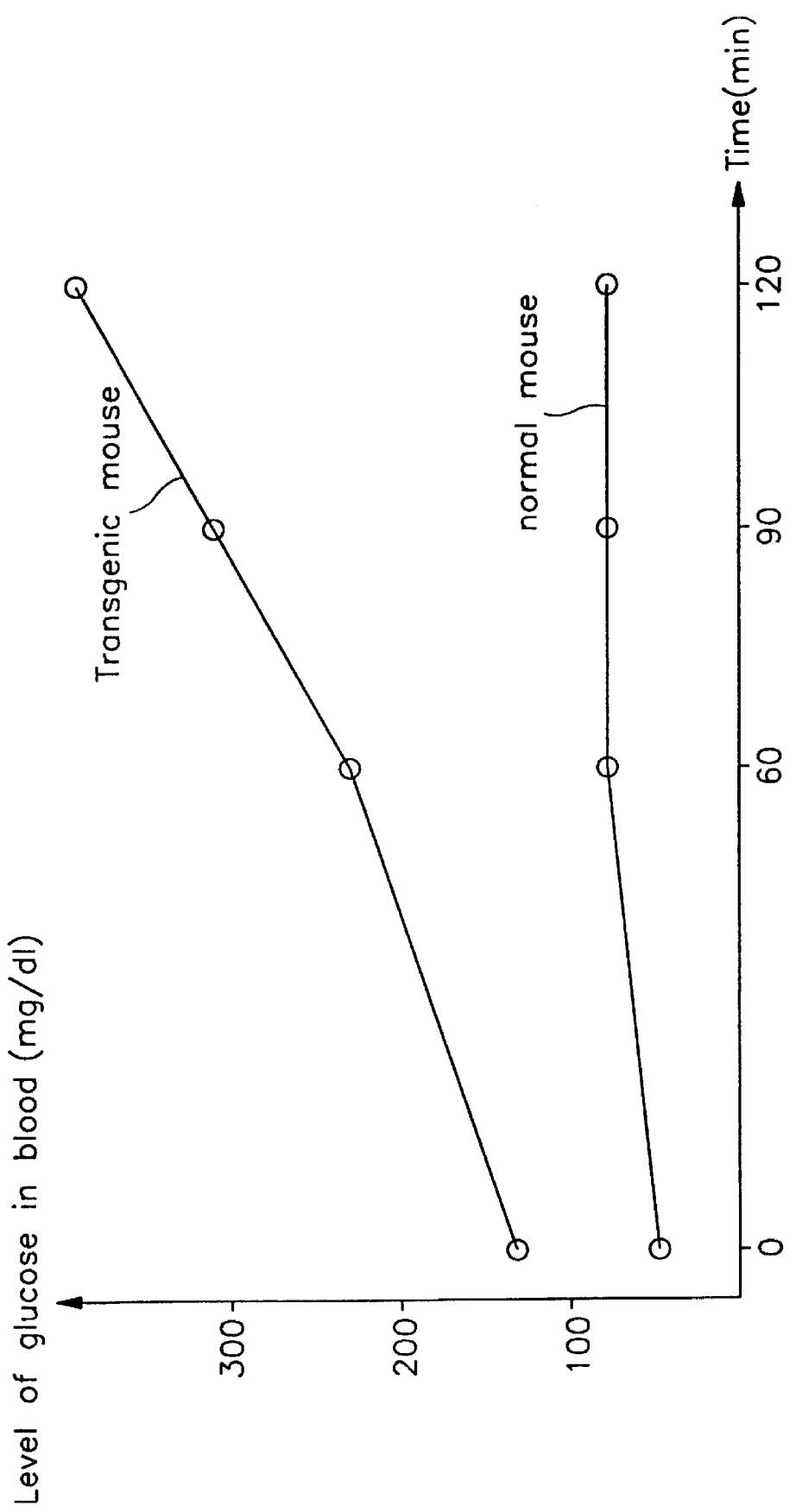
FIG. 4 shows the results of glucose tolerance test of the transgenic mouse.

In order to detect whether a transgenic mouse suffered from diabetes or not, 5 mg of sugar was administered to both a normal mouse and a transgenic mouse, and blood glucose level determined in the two mice at intervals of 0, 60, 90 and 120 minutes respectively, as shown in FIG. 4. The normal mouse maintained a level of blood glucose of 100 mg/dl or less of glucose in blood however, the blood glucose level in the transgenic mouse was highly increased with lapse of time to a level of 300 mg/dl. Therefore, it can be seen that a transgenic mouse suffered from diabetes.

4) Pathological assay of pancreas

Figure 5A:
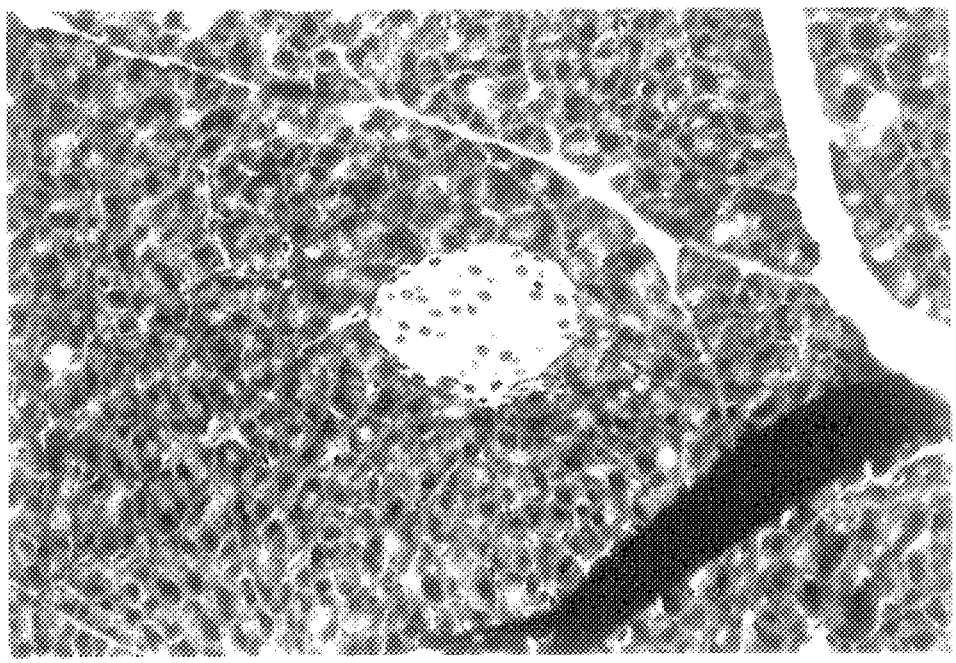
FIGS. 5a and 5b show photographs of pancreas tissues of normal mouse and the transgenic mouse, respectively.
Figure 5B:
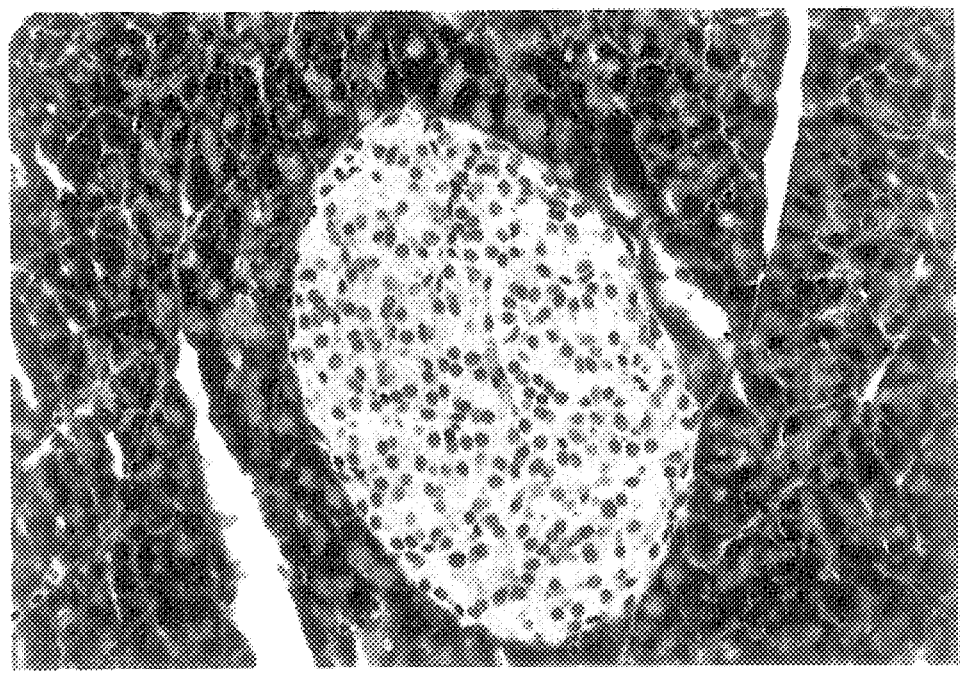

A standard 5-um section of pancreas was fixed in 4 paraformaldehyde, embedded paraffin, stained with haematoxylin in a conventional manner. The photographs of result thereof are shown in FIG. 5, where a is a 200 times enlarged photo of control pancreas, b is a 200 times enlarged photo of pancreas of transgenic mouse. It can be shown that pancreas islet of diabetes-inducing transgenic mouse was excessive proliferated compared with normal pancreas islet.

As pancreas islets were excessive proliferated, it can be assumed that the transgenic mouse suffered from non-insulin diabetes.

What is claimed is:

1. An non-insulin dependent diabetes-inducible transgenic mouse, wherein the germ cells and somatic cells of said mouse comprise recombinant DNA consisting of a 1.8 kb EcoRI-BamHI fragment of a human insulin gene promoter operably linked to a 2.3 kb BamHI-HindIII fragment of human heat shock protein 70 gene, and wherein expression of said human heat shock protein 70 in said mouse results in said mouse exhibiting elevated levels of blood glucose and an enlarged pancreas in response to the administration of sugar.

2. A transgenic mouse according to claim 1, wherein said human heat shock protein 70 is expressed in pancreatic β cells of said transgenic mouse resulting in said mouse exhibiting an excessively proliferated pancreas.

3. A process for preparing the transgenic mouse of claim 1, comprising the steps of:

(I) introducing recombinant DNA consisting of a 1.8 kb EcoRI-BamHI fragment of a human insulin gene promoter operably linked to a 2.3 kb BamHI-HindIII fragment of human heat shock protein 70 gene into a fertilized egg or embryo of a mouse, (ii) inserting said egg or said embryo into the uterus of a foster mother mouse;

(iii) allowing said egg or said embryo to develop to term;

(iv) obtaining a founder mouse carrying said recombinant DNA; and (v) breeding said founder mouse with a normal mouse to obtain F1 offspring that express the human heat shock protein 70, and wherein said F1 offspring exhibit elevated levels of blood glucose and an enlarged pancreas in response to the administration of sugar.

4. The process of claim 3, wherein said recombinant DNA is introduced into a mouse embryo.

5. The process of claim 3, wherein said recombinant DNA is introduced into a fertilized mouse egg.

6. The process of claim 3, further comprising the steps of:

(I) mating two of said F1 offspring to obtain a homozygous transgenic mouse that expresses the human heat shock protein 70, and wherein said homozygous transgenic mouse exhibits elevated levels of blood glucose and an enlarged pancreas in response to the administration of sugar.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GCAGGTGTGT AACCCCATCA TCAGCGGA        2 8

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
TTCCGGTTTC  TACATGCAGA  GATGAATT                                                                28
```

( 2 ) INFORMATION FOR SEQ ID NO:3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
GCGGGTGTGC  AGCCCCATCA  TCAGTGGG                                                                28
```

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
TTAAGGTAAT  TGCGTTGACT  GTTAAATT                                                                28
```